(12) United States Patent
Sain et al.

(10) Patent No.: US 7,943,349 B2
(45) Date of Patent: May 17, 2011

(54) **MODIFIED THERMOPLASTIC STARCH FROM *OPHIOSTOMA ULMI* POLYSACCHARIDE CONVERSION**

(76) Inventors: Mohini Sain, Toronto (CA); Robert Jeng, North York (CA); Martin Hubbes, North York (CA)

( * ) Notice: Subject to any disclaimer, the term of this patent is extended or adjusted under 35 U.S.C. 154(b) by 923 days.

(21) Appl. No.: 11/764,683

(22) Filed: Jun. 18, 2007

(65) Prior Publication Data

US 2008/0308965 A1 Dec. 18, 2008

(51) Int. Cl.
*C12P 19/04* (2006.01)

(52) U.S. Cl. ..... 435/101; 435/100; 435/171; 435/254.1; 127/71; 536/1.11

(58) Field of Classification Search .......... 435/100, 435/101, 171, 254.1; 127/71; 536/1.11
See application file for complete search history.

(56) References Cited

U.S. PATENT DOCUMENTS

| | | |
|---|---|---|
| 5,397,834 A | 3/1995 | Jane et al. |
| 5,407,979 A | 4/1995 | Wu et al. |
| 5,437,924 A | 8/1995 | Decker, III et al. |
| 5,922,379 A | 7/1999 | Wang |
| 6,119,567 A | 9/2000 | Schindler et al. |
| 6,235,815 B1 | 5/2001 | Loercks et al. |
| 6,323,265 B1 | 11/2001 | Bengs et al. |
| 6,365,079 B1 | 4/2002 | Winkler et al. |
| 6,376,583 B1 | 4/2002 | Winkler et al. |
| 6,472,497 B2 | 10/2002 | Loercks et al. |
| 6,559,244 B1 | 5/2003 | Sodergard et al. |
| 7,067,651 B2 | 6/2006 | Poovarodom et al. |

OTHER PUBLICATIONS

Huang et al. BioResource (Nov. 2006) 1(2): 257-269.*
Dennenberg et al. J. Applied Polymer Sci. (1978) 22: 459-465.*
Roldan-Carrillo et al. Bioresource Technology (2003) 86: 1-5.*
Zheng et al. Wuhan Daxue Xuebao, Ziran Kexueban (2000) 46(4): 449-452 (abstract only).*
Jeng et al. For. Path. (2007) 37: 80-95.*
The website www.formedium.com/uk/FusariumSP.htm for the content of potato dextorse broth downloaded Dec. 31, 2010.*

* cited by examiner

*Primary Examiner* — Sandra Saucier
*Assistant Examiner* — Susan Hanley

(57) ABSTRACT

A novel modified thermoplastic starch is manufactured from a native starch using a polysaccharide produced by the fungus species *Ophiostoma ulmi*, by growing a culture in a yeast extract medium; adding the native starch; mixing, and harvesting the modified thermoplastic starch. The modified thermoplastic starch may be used in the manufacture of a biodegradable plastic which exhibits low water absorbency and high tensile strength. The plastic may be used to manufacture films or molding products by casting, extrusion, injection, or compression techniques.

20 Claims, 8 Drawing Sheets

MODIFIED THERMOPLASTIC STARCH FROM OPHIOSTOMA ULMI POLYSACCHARIDE CONVERSION

TECHNICAL FIELD

The present invention relates to biodegradable plastics. In particular, the present invention relates to modified starch-based biodegradable plastics.

BACKGROUND OF THE INVENTION

An increased emphasis on sustainability, eco-efficiency, and green chemistry has driven a search for renewable and environmentally friendly resources. Starch is a biodegradable polysaccharide, produced in abundance at low cost, which exhibits thermoplastic behaviour. Therefore, it has become one of the most promising candidates for an alternative material to replace traditional plastics in certain market segments such as the food packaging industry.

Numerous studies have been conducted to optimize the performance of starch-based plastics (Mali, S. et al. (2004), *Food Hydrocolloids*, 19 (2005), 157-164); Soest, J. et al. (1997), *Trends in Biotechnology*, 15(6), 208-213; Fama, L. et al., *LWT*, 38, 631-639; Lawton, J. W. (1996), *Carbohydrate Polymers,* 29 (1996), 203-208). These studies have shown that important properties for evaluation of a packaging material include mechanical properties, gas and water vapour permeability, thermoforming properties, resistance, transparency, and availability (Weber, C. et al. (2001), *Food Additives and Contaminants,* 19, Supplement, 172-177).

However, the design and engineering of a starch-based packaging product that possesses all of these required properties is a significant challenge. Difficulties are encountered with cost, technical hurdles such as brittleness associated with high loads, and poor water and gas barrier properties which must be overcome to commercialize the biomaterial (Lorcks, J. (1997), *Polymer Degradation and Stability,* 59 (1998), 245-249).

Other studies have modified the functional properties of starch to enhance its inherent bonding strength by focusing on incorporating additives such as plasticizers to improve the performance of the material (Poutanen, K. et al. (1996), *TRIP* 4-4 (1996), 128-132; Laohakunjit, N. et al. (2003), *Starch,* 56 (2004), 348-356).

It has also been reported that certain fungi have the ability to produce exo-polysaccharides that have great potential for use in cosmetic and food industries because of their bioactive characteristics, rheological behavior, and high stability at high temperature (Selbmann, L. et al. (2003), *Antonie Van Leeuwenhoek,* 84 (2003), 135-145).

SUMMARY OF THE INVENTION

According to one embodiment of a method of the present invention, there is provided a method of manufacture of a modified thermoplastic starch from a native starch using a polysaccharide produced by a fungus species, comprising the steps of: growing a culture of the fungus species in a fungal growth medium as a shake culture at an agitation rate sufficient to optimize fungal growth for a time period of between 0.5 and 10 days, preferably between 0.5 and 5 days, until the concentration of spores of the fungus species is between 0.1 and 10 g/L; adding the native starch to the fungus species culture to form a mixture; mixing the mixture at a rate of between 10 and 1000 rpm, preferably at a rate of between 10 and 500 rpm, and a mixing temperature of between 5° C. and 50° C., preferably between 5° C. and 40° C.; and harvesting the modified thermoplastic starch.

The native starch may be selected from the group comprising native potato starch, native corn starch, and native tapioca starch. The fungus may be *Ophiostoma* sp. or related *Ascomycetes* sp. The *Ophiostoma* sp. may be *Ophiostoma ulmi* sensu lata (*O. ulmi* and *O. novo-ulmi*).

The fungal growth medium may be a yeast extract medium. The yeast extract medium may comprise DIFCO® yeast extract, $KH_2PO4$, $MgSO_4$, $FeCl_3.6H_2O$, $MnCl_4.H_2O$, $ZnSO_4.7H_2O$ and sucrose, in distilled water.

According to one embodiment, the harvesting step may comprise extraction of the modified thermoplastic starch and lyophilization. According to an alternative embodiment, the harvesting step may comprise the following steps: centrifuging the spore culture at between 10 and 10000 rpm, preferably at between 200 and 6000 rpm for a centrifugation period of between 0.5 and 60 minutes, preferably between 5 and 40 minutes, at room temperature to obtain a supernatant; decanting the supernatant; lyophilizing the remaining mixture until dry; and removing the dried spores.

According to another embodiment of a method of the present invention, the step of adding the native starch may be replaced with the following steps: centrifuging the fungus species culture at high speed to obtain a supernatant; and incubating the supernatant with the native starch for between 0.1 and 10 days, preferably between 0.1 and 4 days.

According to yet another embodiment of a method of the present invention, the fungal growth culture medium may contain native starch, and the following additional steps after growth of the spore cultures may be employed: centrifuging the mixture at high speed to obtain a supernatant; adding ethanol to the supernatant; centrifuging the mixture at high speed to obtain thermoplastic starch as a precipitate; and isolating the thermoplastic starch.

According to one embodiment, a product of the invention may comprise a modified thermoplastic starch having a tensile strength between 10 and 32 MPa, an elongation at break between 0.5 and 10% and a tensile modulus between 0.3 and 1.5 GPa. Another product of the present invention may comprise a biodegradable plastic.

According to one embodiment, a use of a product of the invention may comprise use of the biodegradable plastic in the manufacture of films or molding products by casting, extrusion, injection, or compression techniques.

According to one embodiment, a use of a product of the invention may comprise use of the modified thermoplastic starch in the manufacture of a biodegradable product selected from the group of products comprising a film exhibiting low water absorbance and high tensile strength, a packaging film, a laminate, a sandwiched material, a foamed molded article, an extruded profile, an insulation material, and a filled molded article.

According to one embodiment, a method of manufacture of a product of the invention may comprise a method of manufacture of a biodegradable plastic containing a modified thermoplastic starch, comprising the steps of: combining the modified thermoplastic starch with glycerol and water in a container; heating the contained mixture in a water bath at about 30° C., preferably at least 70° C., for at least 30 minutes, preferably 1 hour, while maintaining the volume constant, to form a solution; heating the solution at a temperature of at least 30° C., preferably at least 50° C., until a dry plastic is obtained.

BRIEF DESCRIPTION OF THE DRAWINGS

A detailed description of the preferred embodiments is provided by way of example only and with reference to the following drawings, in which:

FIG. 1 illustrates modified thermoplastic starch production after 4 days, according to one embodiment of the present invention;

FIGS. 10A and 110B illustrate Raman mapping of modified thermoplastic potato starch, according to one embodiment of the present invention.

Figure 1:
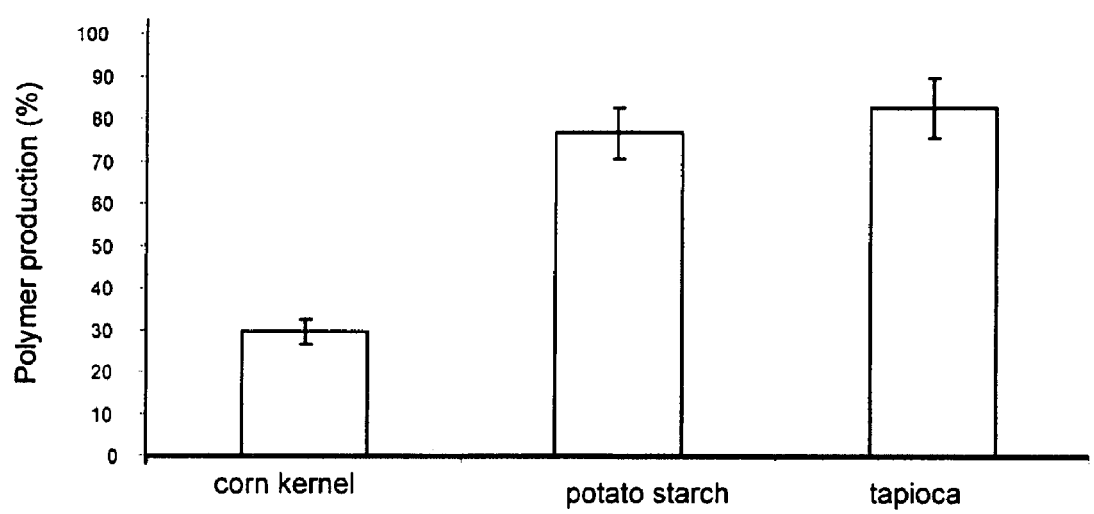

In the drawings, one embodiment of the invention is illustrated by way of example. It is to be expressly understood that the description and drawings are only for the purpose of illustration and as an aid to understanding, and are not intended as a definition of the limits of the invention.

DETAILED DESCRIPTION OF THE INVENTION

*Ophiostoma ulmi* sensu lata ("*O. ulmi*") is the causal agent of Dutch Elm disease. This fungus is unique, as its natural habitat resides in xylem fluid. The inventors have been able to demonstrate that isolates of *O. ulmi* are able to produce exo-polysaccharides in a culture medium (.Jeng, R., et al. (2007), *Forest Pathology*, 37: 80-95). When starch is used as the substrate in *O. ulmi* culture, a biopolymer is produced that shows characteristics well suited to a bio-packaging material.

There is disclosed a commercially viable process for large scale production of a biopolymer which can be used as packaging material for a variety of applications.

The modified thermoplastic starch of the invention is obtained by incubating the spores and/or mycelia of *O. ulmi* in a culture medium containing starch, yeast extract, micronutrients and sucrose. The starch may be potato starch, corn starch or tapioca starch.

Two starch conversion methods are disclosed. According to the first, the ethanol precipitation conversion method, *O. ulmi* is added to a yeast extract medium containing native starch to a desired spore concentration and incubated for a desired period of time. Ethanol precipitation of the incubated mixture and drying of the precipitate produces a novel thermoplastic starch. The rate of native starch conversion can be optimized through selection of spore concentration and incubation time.

According to one embodiment of an ethanol precipitation starch conversion method of the invention, the conversion medium contains, per liter of distilled water, 2.0 g/L DIFCO® yeast extract, 1.0 g/L $KH_2PO_4$, 0.1 g/L $MgSO_4$, 0.48 mg/L $FeCl_3.6H_2O$, 0.36 mg/L $MnCl_4.H_2O$, 0.44 mg/L $ZnSO_4.7H_2O$ and 10 g/L sucrose, ("YE medium"). 25 g/L native starch is added to the YE medium. 200 mL of 0. *ulmi* isolate is added to the medium to a concentration of fungal spores of between 3.5 and 4.0 g/L (dry weight). The mixture is incubated on an orbiting shaker at a speed of 150 rpm for between 2 and 5 days at room temperature. Modified thermoplastic starch is obtained by ethanol precipitation using an equal amount of 95% ethanol. The modified thermoplastic starch precipitate is freeze-dried or air-dried. The rate of starch conversion may be optimized by selection of spore concentration and incubation time.

According to one embodiment of a non-ethanol precipitation starch conversion method from spore-containing culture, according to the invention, *O. ulmi* is grown in a 4 L flask containing 2 L of YE medium. Two isolates (W9 and Q412) of *O. ulmi* are used as a model system, but other isolates would also be acceptable. The spore culture is maintained at room temperature as a shake culture at 150 rpm for 5 days, until the concentration of fungal spores is 3.5 to 4 g/L (dry weight). To initiate starch conversion, 450 g of starch was added to the YE media containing spores. The starch may be steam autoclaved. The mixture is placed on orbiting shaker at speed of 150 rpm at room temperature. Modified thermoplastic starch may be harvested by either of two different methods.

According to a first harvest method, fungal spores are not removed. Modified thermoplastic starch is harvested through filtration and lyophilized without additional treatment. According to a second harvest method, the mixture is centrifuged at 5000 rpm for 25 minutes at room temperature. The supernatant is discarded and the mixture lyophilized until dry. Dried spores are removed and discarded. This second harvest method produces a modified thermoplastic starch which provides increased clarity and improved mechanical properties in a film.

According to one embodiment of a non-ethanol precipitation starch conversion method from spore-free culture, according to the invention, *O. ulmi* is grown in a 4 L flask containing 2 L of YE medium. Two isolates (W9 and Q412) of *O. ulmi* are used as a model system, but other isolates would also be acceptable. The spore culture is maintained at room temperature as a shake culture at 150 rpm for 5 days, until the concentration of fungal spores is 3.5 to 4 µL (dry weight). To initiate starch conversion, fungal spores are first removed from the YE medium by high speed centrifugation. The resulting spore-free culture filtrate is mixed with starch and incubated for between 1 and 2 days. Modified thermoplastic starch is obtained by either of the harvest methods previously described.

According to one embodiment of a non-ethanol precipitation starch conversion method from purified exo-polysaccharide, according to the invention, *O. ulmi* is grown in a 4 L flask containing 2 L of YE medium. Two isolates (W9 and Q412) of *O. ulmi* are used as a model system, but other isolates would also be acceptable. The spore culture is maintained at room temperature as a shake culture at 150 rpm for 5 days, until the concentration of fungal spores is 3.5 to 4 g/L (dry weight). Fungal spores are removed from YE medium by high speed centrifugation. Spore-free culture filtrate is mixed with an equal amount of 95% ethanol. Purified exo-polysaccharide is recovered by centrifugation. Precipitated polysaccharide is re-dissolved with water. To initiate starch conversion, 450 g of starch was added to the YE media containing spores. The starch may be steam autoclaved. The mixture is placed on orbiting shaker at speed of 150 rpm at room temperature. Modified thermoplastic starch may be harvested by either of two different methods.

The modified thermoplastic starch of the present invention is a novel polymer which appears to result from the interaction between native starch and exo-polysaccharide produced by *O. ulmi*. A biodegradable film made by blending the modified thermoplastic starch in a mixture of glycerine and water exhibits low water absorbance and high strength in tensile and modulus tests.

The film is formulated by combining 8.0 g modified thermoplastic starch with 3.95 g glycerol in a 300 mL beaker, and adding approximately 150 ml water. The suspension is heated in a 90° C. water bath for 1 hour, while maintaining a constant volume by adding water. The solution is poured into a 15 cm diameter Petri-dish. According to the ethanol precipitation method, the dish is left to evaporate at room temperature. According to the non-ethanol methods, the dish is dried in a 50° C. oven. The film is removed from the dish for physical property testing.

For tensile testing, according to test standard ASTM D638, type I, three "dog bone" shaped specimens are cut from each film. Each specimen has a width of 3.00 mm. Each specimen is measured with a caliper for thickness at a minimum of 5 locations. The smallest measurement is recorded as the thickness of the specimen. Most of the specimens have a thickness of between 0.19 mm and 0.26 mm.

Tensile tests are done using a Sintech Universal Tensile Test Machine Model #1. The gage length is 25.4 mm. The specimen is fixed into the slit and pulled apart by the machine at a rate of 2.5 mm/min, until specimen failure occurred. The tensile tests are carried out at 23° C. and 50% relative humidity. The atmosphere of the test site may be climate controlled.

EXPERIMENTAL RESULTS

Experiment 1

Ethanol Precipitated Modified Thermoplastic Starch

Starch Conversion

For ethanol precipitated modified thermoplastic starch, the rate of modified starch conversion using corn starch, potato starch and tapioca starch was measured. Results are shown in FIG. 1, which shows that use of tapioca starch produced the highest conversion rate after 4 days conversion, and corn starch the least. Values depicted in FIG. 1 are mean values with standard deviation as shown, where N=3. By increasing the amount of starch in the medium, a modified starch yield of greater than 85% may be attained.

Water Absorption

Figure 2:
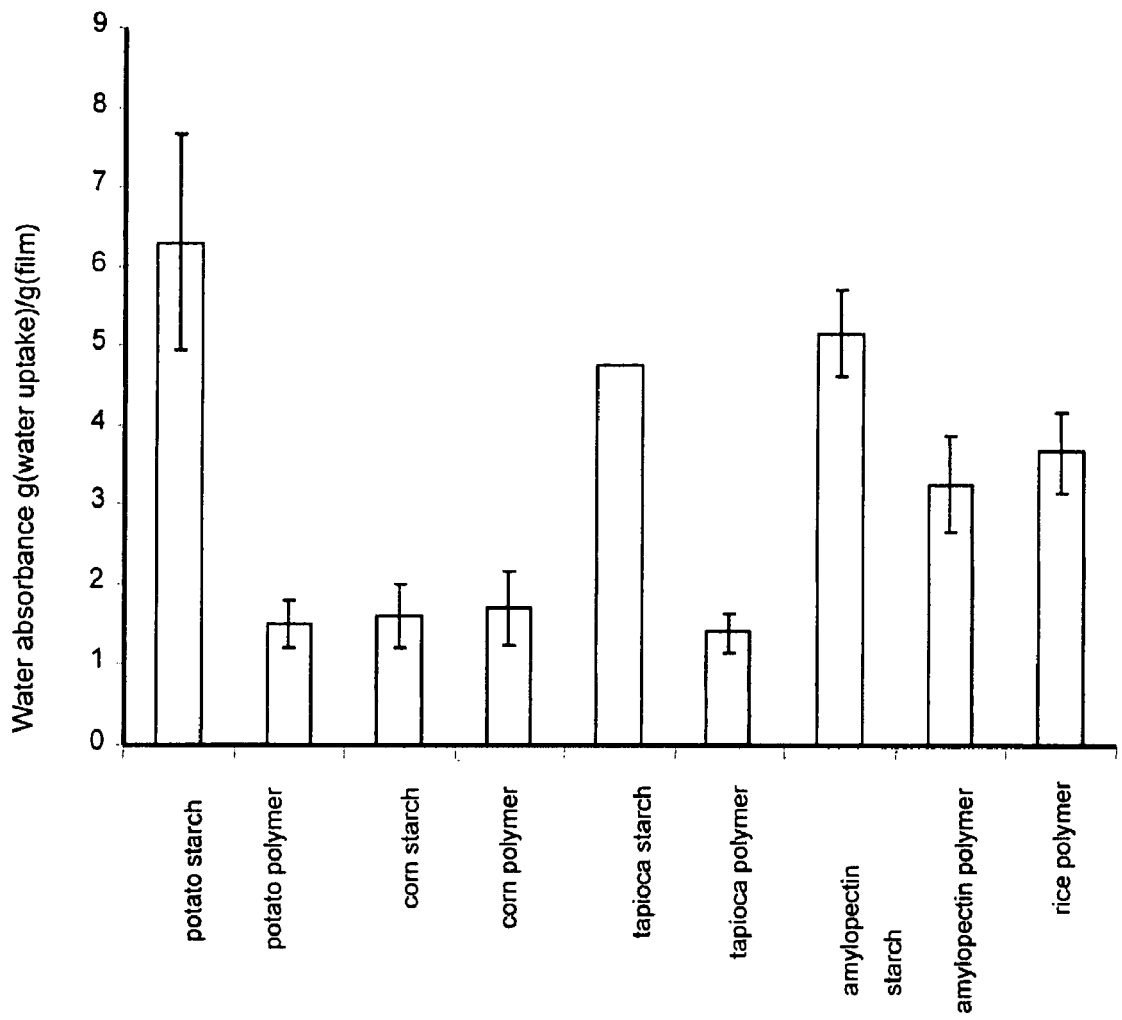
FIG. 2 illustrates water absorbance tests for native starch and modified thermoplastic starch polymer films, according to one embodiment of the present invention.

Films made of native and modified starches from potato, corn, tapioca, amylopectin, and modified rice starch, were soaked in water. As depicted in FIG. 2, after soaking film samples in water, all the unmodified starch films disintegrated within 30 minutes, and continued to absorb water. However, all films made from the modified starch remained intact, even after 24 hours. Furthermore, their water uptake capacities reached a maximum in an hour, and exhibited a plateau thereafter. Values depicted in FIG. 2 are mean values with standard deviation as shown, for N=1 to 3.

After modification, biopolymers derived from potato and tapioca starches exhibited a much lower water absorption, which indicated a higher moisture resistance, a favourable property for packaging material applications.

Tensile Strength

Figure 3:
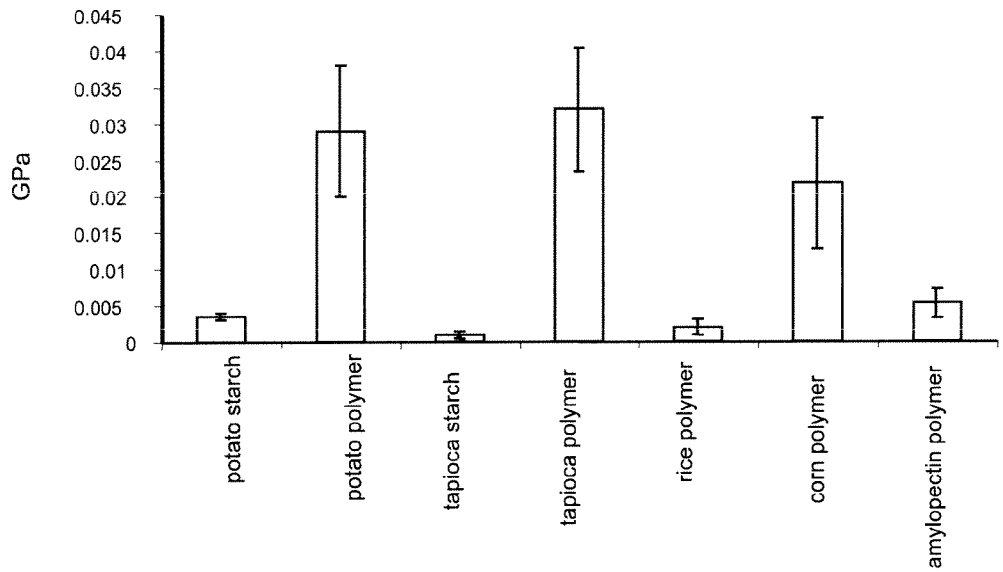
FIG. 3 illustrates tensile modulus of native starch and modified thermoplastic starch polymer films, according to one embodiment of the present invention.

Both native starch and modified thermoplastic starch were cast into films, which were dried at room temperature for at least 3 days, then subjected to tensile testing as described above. As depicted in FIG. 3 and Table I, the experimental results show that the modified starch has improved strength properties and is well suited for use as a packaging material. Tensile modulus values in FIG. 3 are mean values with standard deviation as shown, for N=5, 4, 6, 6, 10, 4 and 3, respectively.

TABLE 1

Tensile Tests of Native and Modified Thermoplastic Starch Films

| | Material | Mean | 95% confidence limits of the mean | | N (number of measurements) |
|---|---|---|---|---|---|
| Peak Stress (MPa) | Potato Starch | 1.60 | 1.18 | 2.01 | 5 |
| | Potato Polymer | 3.58 | 3.22 | 3.92 | 7 |
| | Tapioca Starch | 0.37 | −0.01 | 0.75 | 6 |
| | Tapioca Polymer | 3.60 | 3.30 | 3.89 | 10 |
| | Rice Polymer | 0.43 | −0.04 | 0.89 | 4 |
| | Corn Polymer | 2.52 | 2.14 | 2.90 | 6 |
| | Amylopectin Polymer | 0.97 | 0.44 | 1.51 | 3 |
| Elongation at break (mm) | Potato Starch | 40.78 | 37.05 | 44.50 | 3 |
| | Potato Polymer | 10.78 | 8.34 | 12.31 | 7 |
| | Tapioca Starch | 48.33 | 43.76 | 52.89 | 2 |
| | Tapioca Polymer | 10.77 | 8.73 | 12.81 | 10 |
| | Rice Polymer | 34.79 | 30.22 | 39.35 | 2 |
| | Corn Polymer | 13.36 | 10.73 | 16.00 | 6 |
| | Amylopectin Polymer | 21.72 | 17.16 | 26.28 | 2 |

Figure 4:
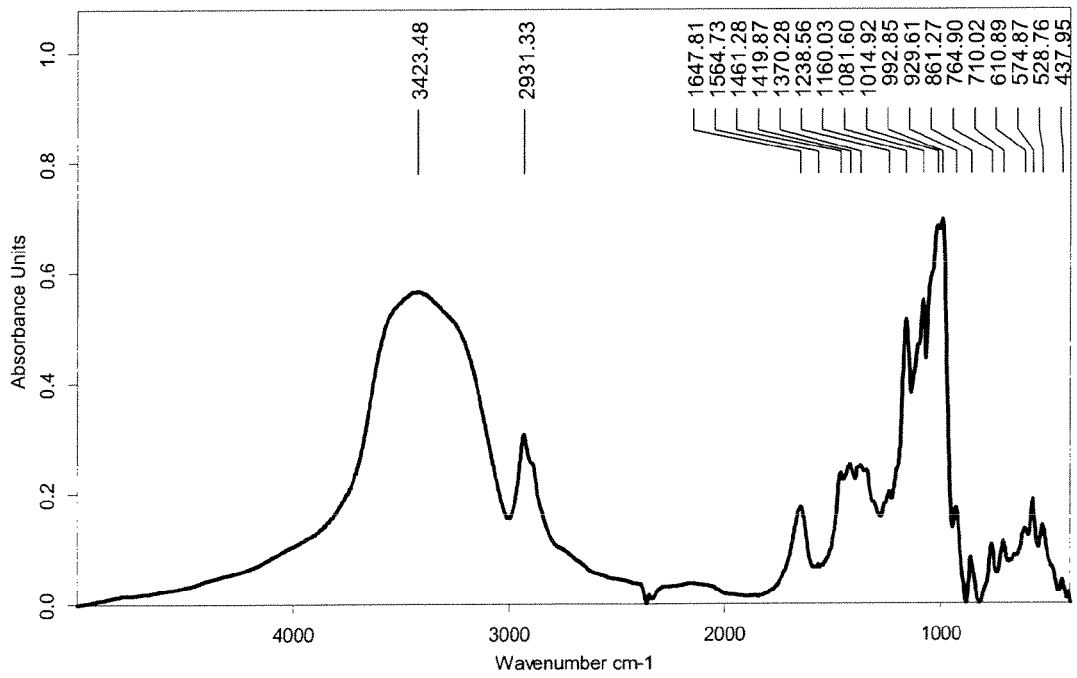
FIG. 4 depicts a Fourier transform infrared ("FT-IR") spectrum of exo-polysaccharide produced by O. ulmi isolate W9, according to one embodiment of the present invention.

Molecular level changes during the modification process were studied by FT-IR. The results are shown in FIG. 4. The spectrum of FIG. 4 represents the native potato starch harvested from the fungal modification of native potato starch.

The experimental results clearly indicate that isolates of *O. ulmi* can modify native starch into a new polymer which produces a bio-film having low water absorbance and high mechanical strength. Changes in the starch structure may be studied through FT-IR. The pyranose ring is maintained after the modification, but the strength of the hydrogen bonds between molecules is intensified. Peak shifts and ratio changes suggest the fixation of new chemical functional groups or new linkages between starch molecules. Peaks at 798.09 $cm^{-1}$, 1257.71 $cm^{-1}$ and 2860.65 $cm^{-1}$ are characteristic of the modified thermoplastic starches.

Based on these results, two possible pathways of the modification are suggested. One pathway may involve the fungus *O. ulmi* producing a polymer which can bond starch molecules together and form new cross-linked structures. The second possible pathway may involve the fungus attaching to one or more functional groups which help strengthen the starch polymer.

Non-Ethanol Precipitated Modified Thermoplastic Starch

Experiments were carried out to determine parameters required for large scale production and improved mechanical strength of bio-films. *O. ulmi* isolates W9 and Q412 were both tested. Results are reported based on tensile testing of bio-film made from modified thermoplastic potato. The method for film casting is as described previously.

Direct Harvest Method from Spore-containing Culture

For modified thermoplastic starch film derived by the direct harvest method from spore-containing culture, several experiments were carried out.

Experiment 2

Non-Ethanol Precipitation With Room Temperature Drying

In this experiment, the film was dried at room temperature and tensile testing was performed after 5 days. A W9 isolate was used. The results are shown in Table 2.

TABLE 2

Tensile testing of modified and unmodified starch films

| Sample | peak stress | | elongation | | modulus | |
|---|---|---|---|---|---|---|
| | mean | SD | mean | SD | mean | SD |
| Unmodified starch | 2.640 | 0.060 | 8.960 | 0.470 | 0.023 | 0.001 |
| W day 1 | 14.310 | 4.144 | 2.658 | 1.372 | 0.871 | 0.286 |
| W day 2 | 9.184 | 1.446 | 5.748 | 1.230 | 0.369 | 0.097 |
| W day 3 | 7.442 | 1.573 | 9.596 | 2.045 | 0.215 | 0.109 |
| W day 4 | 11.617 | 5.243 | 0.403 | 1.139 | 0.339 | 0.277 |
| W day 5 | 6.954 | 1.627 | 7.687 | 1.650 | 0.210 | 0.095 |
| W day 6 | 2.200 | 0.190 | 9.080 | 0.660 | 0.017 | 0.001 |
| W day 7 | 2.050 | 0.000 | 9.260 | 0.000 | 0.018 | 0.000 |
| W day 8 | 2.360 | 0.040 | 9.120 | 0.310 | 0.027 | 0.007 |

Experiment 3

Non-Ethanol Precipitation of Q412 Isolate With 50° C. Drying

In this experiment, the film was dried at 50° C. for 24 hours. Tensile testing was performed after the film was brought back to room temperature. A Q412 isolate was used, with native starch as a control. Ethanol precipitated modified thermoplastic starch is included as reference. The results are shown in Table 3.

TABLE 3

Tensile testing of Q412 isolate with 50° C. Drying

| Sample | peak stress | | elongation | | modulus | |
|---|---|---|---|---|---|---|
| | mean | SD | mean | SD | mean | SD |
| Control | 2.28 | | 21.7 | | 0.0353 | |
| Q22 hr. | 6.32 | 1.9721 | 11.05 | 2.803 | 0.3768 | 0.208 |
| Q24 hr. | 7.18 | 0.0987 | 9.67 | 1.1372 | 0.3429 | 0.059 |
| Q d2 | 8.51 | 0.9551 | 7.33 | 1.2527 | 0.4978 | 0.0882 |
| Q d3 | 10.6 | 0.5052 | 6.73 | 0.7506 | 0.6483 | 0.1071 |
| Q d4 | 11.08 | 1.8608 | 6.23 | 1.159 | 0.7694 | 0.1126 |
| Q d5 | 10 | 2.4676 | 6.93 | 2.6725 | 0.5459 | 0.2076 |
| Q d6 | 6.95 | 0.2949 | 11.37 | 0.4509 | 0.2532 | 0.0451 |
| Q d7 | 9.12 | 0.3164 | 7.47 | 0.9504 | 0.4308 | 0.0998 |
| Q d8 | 8.92 | 0.3913 | 6.27 | 1.3317 | 0.4978 | 0.0929 |
| ETOH | 11.49 | 1.3931 | 2.23 | 0.7371 | 0.785 | 0.0991 |

Experiment 4

Non-Ethanol Precipitation of W9 Isolate with 50° C. Drying

In this experiment, the film was dried at 50° C. for 24 hours. Tensile testing was performed after film was brought back to room temperature. A W9 isolate was used. Day harvested is indicated with 'd' in the Sample column. The results are shown in Table 4.

TABLE 4

Tensile testing of W9 isolate with 50° C. Drying

| Sample | peak stress | | elongation | | modulus | |
|---|---|---|---|---|---|---|
| | mean | SD | mean | SD | mean | SD |
| W 22 hr. | 14.54 | 0.2307 | 4.77 | 0.671 | 0.9306 | 0.1201 |
| W 24 hr | 8.04 | 0.2996 | 7.28 | 1.0532 | 0.4637 | 0.0861 |
| W d2 | 22.66 | 1.2061 | 2.85 | 0.3514 | 1.3448 | 0.1302 |
| W d3 | 10.42 | 0.6793 | 7.16 | 0.7197 | 0.6875 | 0.0639 |
| W d4 | 17.7 | 1.0382 | 3.45 | 1.002 | 1.223 | 0.0157 |
| W d6 | 11.8 | 0.2601 | 6 | 0.6195 | 0.6982 | 0.1686 |
| W d7 | 10.34 | 0.2109 | 5.83 | 0.7411 | 0.7453 | 0.061 |

Centrifugation Method from Spore-containing Culture

For modified thermoplastic starch film derived by the centrifugation method from spore-containing culture, several experiments were carried out.

Experiment 5

Centrifugation From Spore Culture of Modified Thermoplastic Starch

The film was dried at 50° C. for 24 hours. Tensile testing was performed after film was brought back to room temperature. C represents centrifuged sample, W indicated W9 isolate. The control was native starch. Results are shown in Table 5.

TABLE 5 tensile testing for spore culture of modified thermoplastic starch

| Sample | peak stress | | elongation | | modulus | |
|---|---|---|---|---|---|---|
| | mean | SD | mean | SD | Mean | SD |
| CW d3, | 19.85 | 1.689 | 2.96 | 1.013 | 1.178 | 0.2765 |
| Control | 8.07 | 1.274 | 8.2 | 3.46 | 0.4082 | 0.1368 |

Experiment 6

Time Interval Testing of Modified Thermoplastic Starch Films

A series of films made at the same time were subjected to tensile testing at differing time intervals as described in Table 6. C represents a centrifuged sample. Q indicates a Q142 isolate, W indicates a W9 isolate, 'd' the day harvested. Native starch was used as a control. Results are shown in Table 6.

TABLE 6

Tensile testing with time intervals

| Sample | peak stress mean | SD | elongation mean | SD | modulus mean | SD | treatment |
|---|---|---|---|---|---|---|---|
| CQ d1 | 11.81 | 1.3 | 6.5 | 2.893 | 0.6392 | 0.1588 | 50° C. for 24 hr |
|  | 25.21 | 2.6 | 2.38 | 1.226 | 1.088 | 0.315 | 50° C. for 48 hrs |
|  | 8.53 | 0.66 | 10.44 | 1.543 | 0.4835 | 0.2373 | To RT after 48 hr |
| CQ d2 | 21.31 |  | 3.75 |  | 1.276 |  | 50° C. for 24 hr |
|  | 23.79 | 2.03 | 2.083 | 1.105 | 1.505 | 0.042 | 50° C. for 48 hrs |
| CQ d2 | 9.34 | 0.61 | 8.53 | 1.572 | 0.6249 | 0.1785 | 50° C. for 48 hrs |
| CQ d1 | 22.89 | 1.7 | 2.483 | 1.182 | 1.087 | 0.028 | 50° C. for 48 hrs |
|  | 8.37 |  | 9.9 |  | 0.5516 |  | To RT after 48 hr |
| CW d3 | 19.85 | 1.689 | 2.96 | 1.013 | 1.178 | 0.2765 | 50° C. for 48 hrs |
| CW d3 wash | 11.55 | 3.51 | 6.2 | 3.203 | 0.5995 | 0.0656 | 50° C. for 48 hrs and water wash after centrifugation |
| CW d1 | 8.62 | 1.36 | 11.1 | 0.9019 | 0.5734 | 0.1771 | 50° C. for 24 hr |
|  | 14.41 | 3.14 | 6.673 | 1.107 | 0.8362 | 0.3666 | 50° C. for 48 hrs |
|  | 6.17 | 1.1 | 16.1 | 2.4 | 0.2438 | 0.0714 | To RT after 48 hr |
| Control | 5.79 | 0.58 | 14.66 | 2.74 | 0.3352 | 0.0325 | 50° C. for 48 hrs |
|  | 3.32 | 0.03 | 15.71 | 1.64 | 0.1003 | 0.029 | To RT after 48 hr |

Experiment 7

Time Interval Testing of Modified Thermoplastic Starch Films

A series of films made at the same time were subjected to tensile testing at differing time intervals as described in Table 7. C represents a centrifuged sample. W indicates a W9 isolate, 'd' the day harvested. Native starch was used as a control. Results are shown in Table 7.

TABLE 7

Time interval testing of modified thermoplastic starch films

| Sample | peak stress mean | SD | elongation mean | SD | modulus mean | SD | treatment |
|---|---|---|---|---|---|---|---|
| CW d1 | 16.79 | 2.069 | 1.12 | 0.485 | 0.8174 | 0.2116 | 50° C. for 24 hr |
|  | 24.38 | 3.44 | 2.95 | 1.195 | 1.357 | 0.161 | 50° C. for 48 hrs |
| CW d2 | 15.32 | 0.87 | 4.95 | 1.062 | 0.948 | 0.143 | 50° C. for 24 hr |
|  | 22.69 |  | 3.63 |  | 1.255 |  | 50° C. for 48 hrs |

In order to increase the yield of modified thermoplastic starch, 450 g of native potato starch, instead of 225 g, was added to 1 L of YE media. The amount of spores and the procedures for film casting are the same as previously described. The results are as set out in Tables 8, 9 and 10

Experiment 8

Tensile strength at Time Intervals for Q412 Isolate

A series of films made at the same time were subjected to tensile testing at differing time intervals as described in Table 8. C represents a centrifuged sample. Q indicates a Q412 isolate. 'd' the day harvested. Native starch was used as a control. Results are shown in Table 8.

TABLE 8

Tensile strength at time intervals for Q412 isolate

| Sample | peak stress mean | SD | elongation mean | SD | modulus mean | SD | treatment |
|---|---|---|---|---|---|---|---|
| CQ d1 | 27.26 | 0.56 | 1.939 | 0.178 | 1.505 | 0.086 | 50° C. for 24 hr |
|  | 25.33 | 2.59 | 0.646 | 0.296 | 1.604 | 0.185 | 50° C. for 48 hrs |
|  | 18.43 | 2.17 | 1.34 | 0.15 | 1.279 | 0.088 | To RT after 48 hr |
| CQ d2 | 22.93 | 1.38 | 2.73 | 0.151 | 1.239 | 0.0509 | 50° C. for 24 hr |
|  | 23.59 | 4.24 | 2.291 | 1.142 | 1.359 | 0.172 | 50° C. for 48 hrs |
|  | 13.85 | 5.02 | 5.48 | 3.207 | 0.8721 | 0.3481 | To RT after 48 hr |

Experiment 9

Tensile Strength at Time Intervals for W9 Isolate

A series of films made at the same time were subjected to tensile testing at differing time intervals as described in Table 9. C represents a centrifuged sample. W indicates a W9 isolate, 'd' the day harvested. Results are shown in Table 9.

TABLE 9

Tensile strength at time intervals for W9 isolate

| Sample | peak stress mean | SD | elongation mean | SD | modulus mean | SD | treatment |
|---|---|---|---|---|---|---|---|
| CW d1 | 25.24 | 3.13 | 2.8 | 1.122 | 1.254 | 0.203 | 50° C. for 24 hr |
|  | 25.68 | 1.35 | 1.9 | 0.533 | 1.376 | 0.208 | 50° C. for 24 hr |
| CW d1 | 25.44 | 3.31 | 1.87 | 0.872 | 1.292 | 0.072 | 50° C. for 48 hrs |
|  | 26.84 | 2.321 | 2.03 | 0.664 | 1.4813 | 0.0522 | 50° C. for 48 hrs |
| CW d1 | 18.82 | 3.41 | 1.84 | 1.516 | 1.122 | 0.1806 | To RT after 48 hr |

Experiment 10

Tensile Strength at Time Intervals for W9 Isolate

A series of films made at the same time were subjected to tensile testing at differing time intervals as described in Table 10. C represents a centrifuged sample. W indicates a W9 isolate, 'd' the day harvested. Results are shown in Table 10.

TABLE 10

Tensile strength at time intervals for W9 isolate

| Sample | peak stress mean | SD | elongation mean | SD | modulus mean | SD | treatment |
|---|---|---|---|---|---|---|---|
| CW d1 | 25.68 | 1.35 | 1.9 | 0.533 | 1.376 | 0.208 | 50° C. for 24 hr |
|  | 26.84 | 2.321 | 2.03 | 0.664 | 1.4813 | 0.0522 | 50° C. for 48 hrs |
|  | 18.82 | 3.41 | 1.84 | 1.516 | 1.122 | 0.1806 | To RT after 48 hr |

Centrifugation Method from Spore-Free Culture

For modified thermoplastic starch film derived by the centrifugation method from spore-free culture, several experiments were carried out.

Experiment 11

Tensile Strength for Centrifugation Isolation of Modified Thermoplastic Starch

Films made at the same time were subjected to tensile testing at differing time intervals as described in Table 11. C represents a centrifuged sample. Q indicates a Q412 isolate, 'd' the day harvested, –S indicated spores removed before mixing. Results are shown in Table 11.

TABLE 11

Tensile strength for centrifugation isolation of modified thermoplastic starch

| | peak stress | | elongation | | modulus | | |
|---|---|---|---|---|---|---|---|
| Sample | mean | SD | mean | SD | mean | SD | treatment |
| CW-S d1 | 27.17 | 1.01 | 1.8 | 0.183 | 1.524 | 0.055 | 50° C. for 24 hr |
| | 30.82 | 1.76 | 1 | 0.0617 | 1.625 | 0.165 | 50° C. for 48 hrs |
| CW-S d2 | 24.1 | 2.94 | 2.4 | 0.774 | 1.094 | 0.134 | 50° C. for 24 hr |
| | 29.72 | 0.8871 | 1.75 | 0.1935 | 1.454 | 0.1372 | 50° C. for 48 hrs |
| CQ-S d1' | 27.03 | 0.41 | 1.8 | 0.392 | 1.32 | 0.124 | 50° C. for 24 hr |
| | 23.2 | 5.99 | 1.29 | 0.8684 | 1.25 | 0.063 | 50° C. for 48 hrs |
| CQ-Sd2 | 24.84 | 1.11 | 1.92 | 0.678 | 1.383 | 0.189 | 50° C. for 24 hr |
| | 27.99 | 0.8132 | 1.6 | 0.0354 | 1.396 | 0.186 | 50° C. for 48 hrs |

Experiment 12

Tensile Strength for Filtration Isolation of Modified Thermoplastic Starch

Instead of centrifuging, the modified thermoplastic starch was obtained by filtration (F) or both filtration followed by water washing (FW). A series of films made at the same time were subjected to tensile testing at differing time intervals. Q indicates isolate Q412; –S indicates spore removed before mixing, and 2 indicates second set. Results are shown in Table 12.

TABLE 12

Tensile strength for filtration isolation of modified thermoplastic starch

| | peak stress | | elongation | | modulus | | |
|---|---|---|---|---|---|---|---|
| Sample | mean | SD | mean | SD | mean | SD | treatment |
| Q-SF2 | 11.88 | 1.13 | 9 | 1.067 | 0.7305 | 0.0392 | 50° C. for 24 hr |
| Q-SFW2 | 12.49 | 3.79 | 8.1 | 3.661 | 0.7939 | 0.193 | 50° C. for 24 hr |
| Q-SF2 | 14.3 | 2.153 | 8.01 | 1.11 | 0.8167 | 0.0923 | 50° C. for 48 hrs |
| Q-SFW2 | 19.84 | 2.79 | 3.7 | 0.794 | 0.9699 | 0.883 | 50° C. for 48 hrs |
| W SF2 | 11.06 | 0.99 | 9.1 | 0.78 | 0.7305 | 0.0392 | 50° C. for 24 hr |
| W SFW2 | 11.4 | 0.3427 | 8.9 | 0.4583 | 0.4811 | 0.0508 | 50° C. for 24 hr |
| W SF2 | 18.82 | 1.44 | 5.8 | 1.334 | 0.8597 | 0.1101 | 50° C. for 48 hrs |
| W SFW2 | 25.5 | 4.07 | 2.91 | 0.751 | 1.104 | 0.1066 | 50° C. for 48 hrs |
| W-SF | 19.01 | 2.13 | 3.1 | 1.353 | 0.9479 | 0.0655 | 50° C. for 48 hrs |
| W-SFW | 19.59 | 1.44 | 4.6 | 0.217 | 1.049 | 0.046 | 50° C. for 48 hrs |
| W-SF | 14.55 | 0.61 | 4.3 | 0.654 | 0.8751 | 0.0738 | To RT after 48 hr |
| W-SFW | 19.52 | 2.59 | 2 | 1.245 | 1.025 | 0.1065 | To RT after 48 hr |

Experiment 13

Tensile Strength for Non-Autoclaved Modified Thermoplastic Starch

Instead of using autoclaved native starch, the modified thermoplastic starch was obtained by mixing non-autoclaved starch (NAu) with culture filtrate. A series of films made at the same time were subjected to tensile testing at differing time intervals. Q indicates isolate Q412; –S indicates spore removed before mixing. Results are shown in Table 13.

TABLE 13

Tensile strength for non-autoclaved modified thermoplastic starch

| | peak stress | | elongation | | modulus | | |
|---|---|---|---|---|---|---|---|
| Sample | mean | SD | mean | SD | mean | SD | treatment |
| Q-SNAu | 16.84 | 0.71 | 5.9 | 0.583 | 0.9336 | 0.0443 | 50° C. for 24 hr |
| | 27.12 | 1.29 | 2.2 | 0.408 | 1.239 | 0.187 | 50° C. for 48 hrs |

These experiments clearly show that modified thermoplastic starch made from the centrifugation method possesses much better mechanical properties for bio-film. These data also show that the films made from a sample having a longer drying time exhibit high peak stress.

Centrifugation Method from Purified Exo-Polysaccharide

Experiment 14

Tensile Strength for Centrifuged Purified Exo-Polysaccharide

For modified thermoplastic starch film derived by the centrifugation method from purified exo-polysaccharide, tensile testing was carried out. A series of films made at the same time were subjected to tensile testing at differing time intervals. C indicates centrifuged; EPS indicates exo-polysaccharide; and S indicates native starch. Results are shown in Table 14.

TABLE 14

Tensile strength for centrifuged purified exo-polysaccharide

| Sample | peak stress mean | SD | elongation mean | SD | modulus mean | SD | treatment |
|---|---|---|---|---|---|---|---|
| EPS + S + C | 15.63 | 1.22 | 2.58 | 0.6657 | 0.7301 | 0.0136 | 50° C. for 24 hr |
|  | 31.55 | 1.71 | 0.8 | 0.3011 | 1.411 | 0.146 | 50° C. for 48 hrs |

Structural Analysis

Experiment 15

Fourier Transform Infrared Analysis of Modified Thermoplastic Starch

Table 15 shows results of FT-IR testing, a summary of the frequencies and proposed structural assignments of the most characteristic FT-IR bands of the modified thermoplastic starch spectra.

TABLE 15

Fourier Transform Infrared Analysis of Modified Thermoplastic Starch

| Frequency, cm$^{-1}$ | Group Vibration | Intensity IR | Raman | Description |
|---|---|---|---|---|
| 3200-3500 | —OH stretch | very strong | very weak | Hydroxyl |
| 2700-3000 | —C—H stretch | strong-medium | medium | |
| 1640-1650 | H$_2$O | | | |
| 1300-1400 | C—H scissoring | medium | medium-weak | |
| 1300-1350 | C—O stretch | strong | | |
| 300-1300 | | Finger print for skeleton | | |
| 1100-1300 | C—O stretch | strong | medium-weak | |
| 800-900 | Skeletal mode | | medium | α-(1-4) linkage |
| 750-800 | C—O—C skeletal | medium-weak | medium-weak | β-configuration |
| 700-750 | C—O—C skeletal | medium-weak | medium | α-configuration |
| 600-650 | C—H rocking | very strong-medium | very weak | |
| 400-500 | Skeletal mode | | very strong | |

Figure 5:
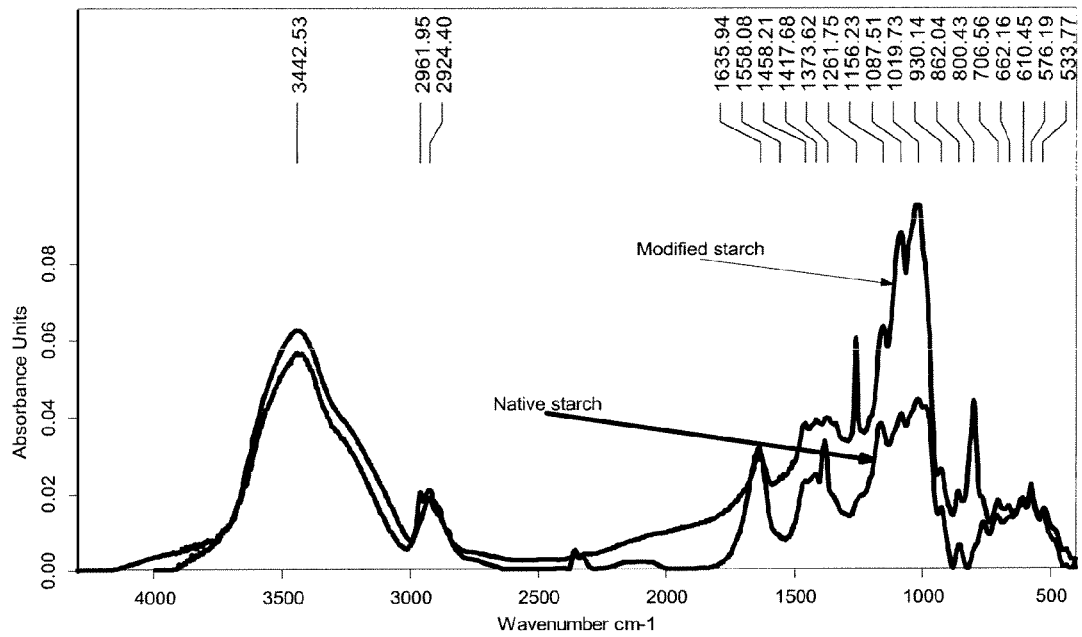
FIG. 5 illustrates FT-IR spectra of unmodified starch, according to one embodiment of the present invention.
Figure 6:
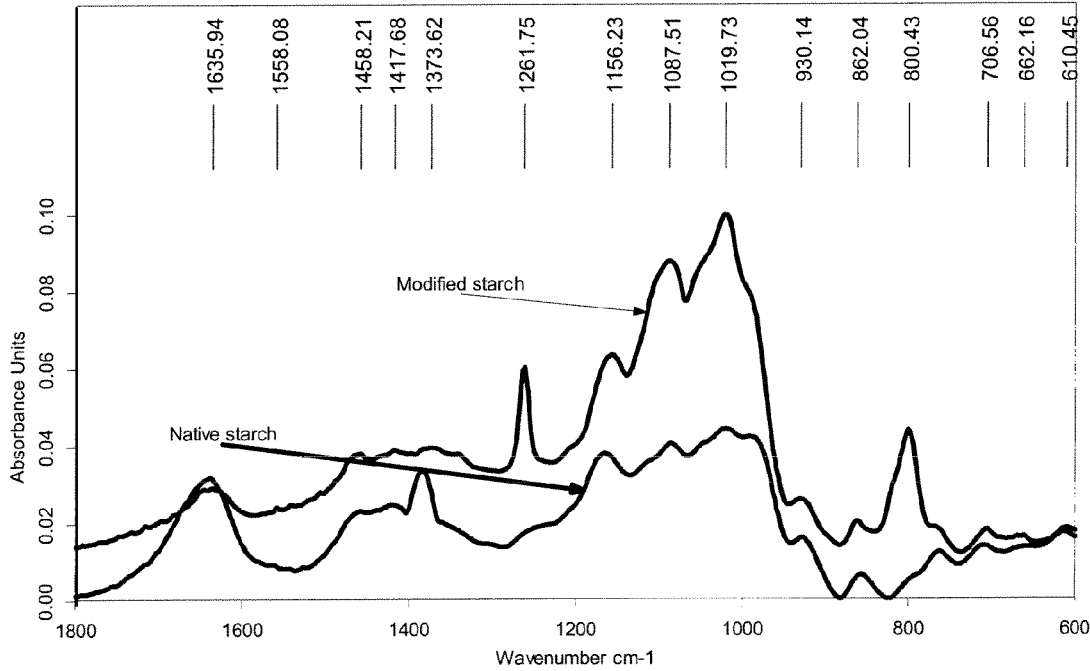
FIG. 6 illustrates detail of FT-IR spectra of unmodified starch and modified thermoplastic starch showing new peaks appearing at 1261.84 and 799.44 $cm^{-1}$ in the modified starch spectrum, according to one embodiment of the present invention.
Figure 7:
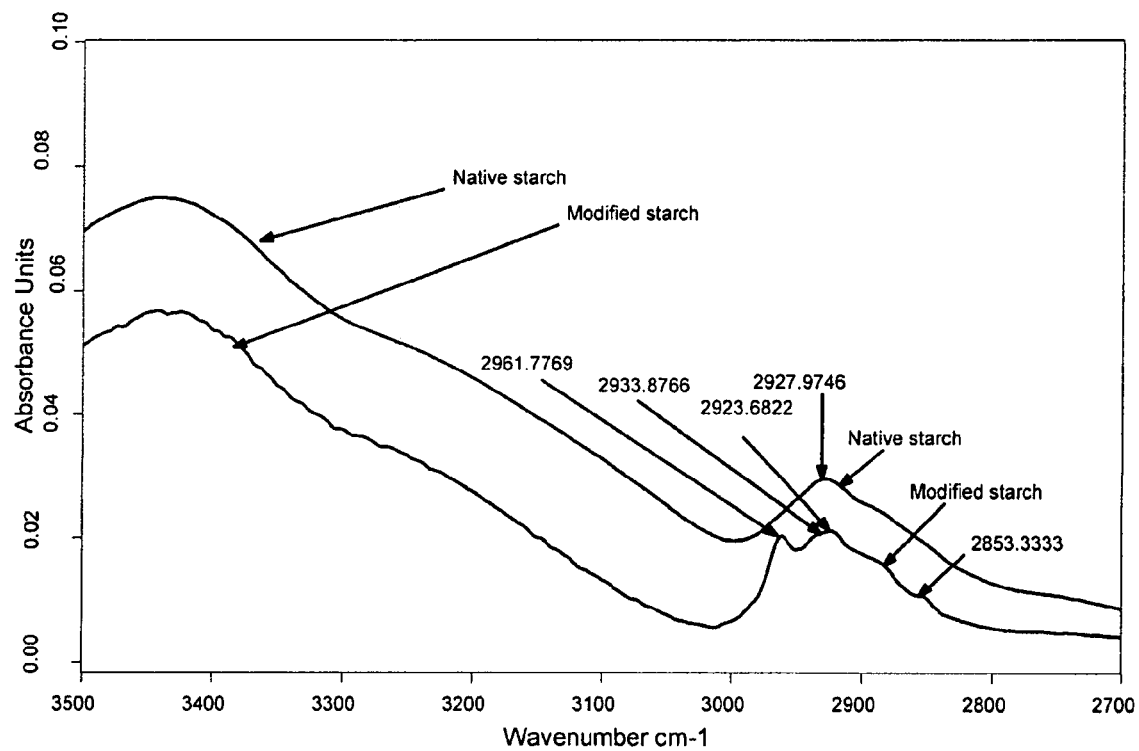
FIG. 7 illustrates detail of FT-IR resonances of unmodified starch and modified thermoplastic starch between 2800 and 3000 $cm^{-1}$, related to C—H stretching, according to one embodiment of the present invention.

The FT-IR spectra are shown in FIGS. 5, 6, and 7. In FIG. 5, new peaks are discernable, and the intensity of the resonances within the spectra, and the resonances at the skeleton mode (400-1500 cm$^{-1}$) are higher compared to resonances due to OH groups in modified starches. FIG. 6 illustrates detail of FT-IR spectrum of UTTS showing two new peaks appearing at 1261.84 and 799.44 cm$^{-1}$. FIG. 7 illustrates detail of FT-IR resonances between 2800 and 3000, related to C—H stretching.

In FIG. 7, a new peak appears at 2961.40 cm$^{-1}$ in modified thermoplastic starches. The peak at 2922.80 cm$^{-1}$ in modified starches may be related to the peak at 2927.19 cm$^{-1}$ in unmodified starches, the shifted peak may be due to a new interaction within the molecular structure of the modified starch.

These figures clearly show the presence of three new peaks in the FT-IR spectrum of the modified thermoplastic starch. These peaks are very similar to those detected in ETOH precipitated modified thermoplastic starch. These peaks may be used as bio-makers for the novel modified thermoplastic starch of the invention.

Figure 8:
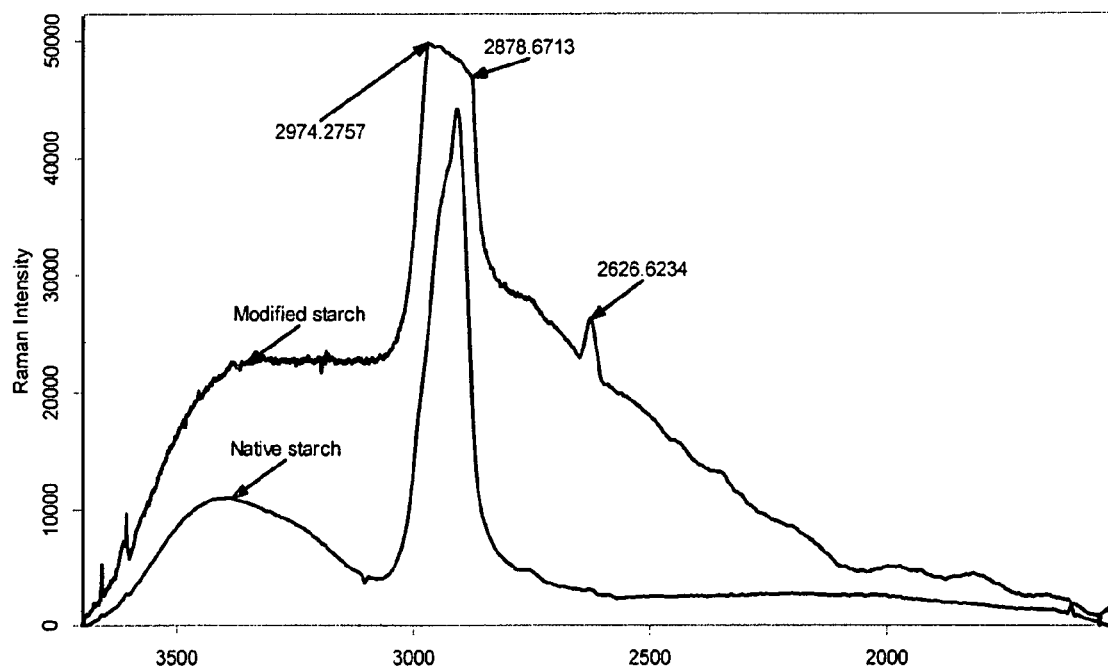
FIG. 8 illustrates Raman spectrum of modified thermoplastic starch and unmodified starch in the spectral range 2000-3500 $cm^{-1}$, according to one embodiment of the present invention.
Figure 9B:
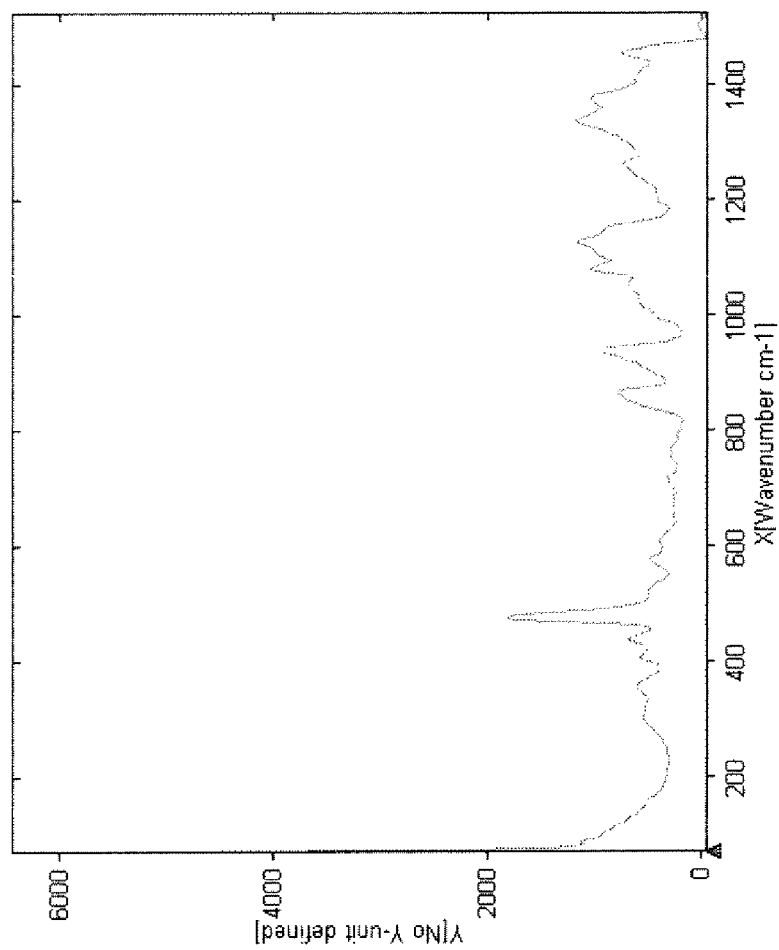
FIGS. 9A and 9B illustrate Raman mapping of native potato starch, according to one embodiment of the present invention.
Figure 9A:
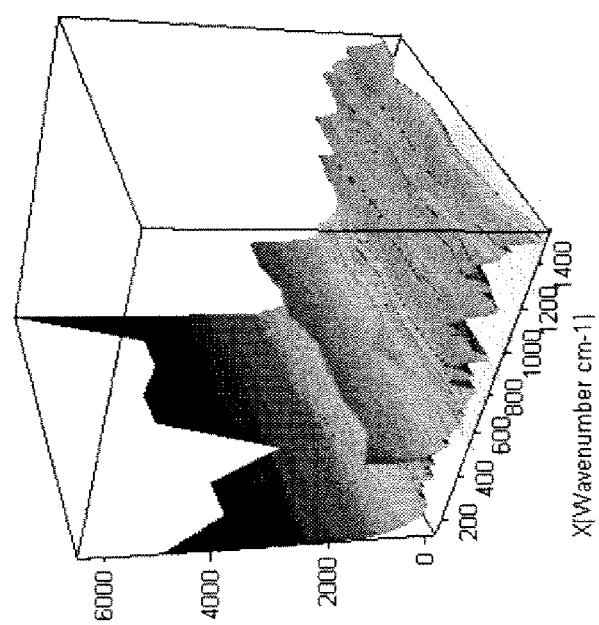
Figures 10A, 10B:
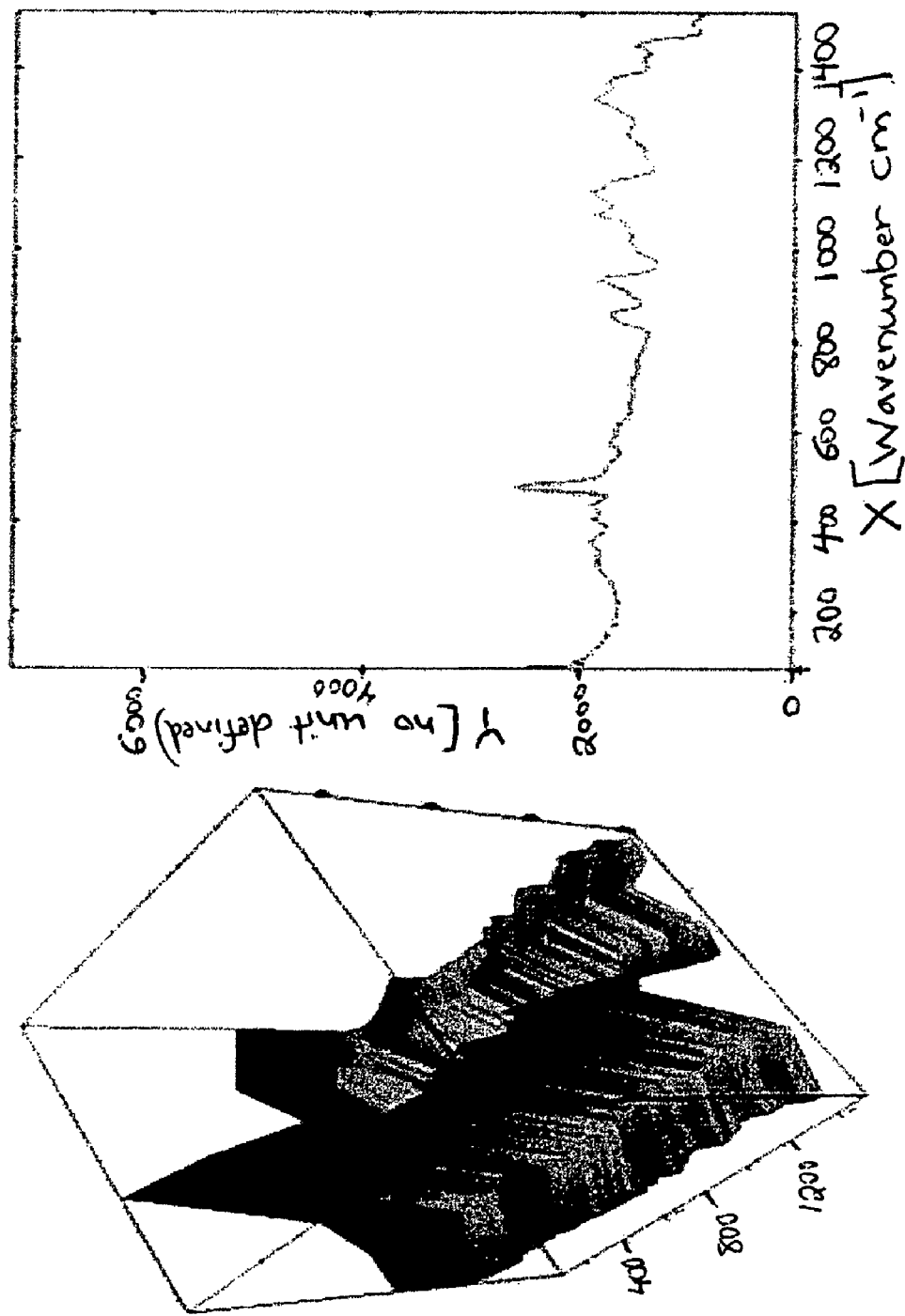

In FIGS. 8, 9A, 9B, 10A and 10B, there are depicted Raman spectra for the modified thermoplastic starch. FIG. 8 illustrates the Raman spectrum of modified thermoplastic starch and native starches, in the spectral range 2000-3500. FIGS. 9A and 9B illustrate Raman mapping and Raman spectrum, respectively, of native potato starches. FIGS. 10A and 10B illustrate Raman mapping and Raman spectrum, respectively, of modified thermoplastic potato starch.

The modified thermoplastic starch of the present invention is a new starch-based thermoplastic resulting from the interaction of native starch and exo-polysaccharide produced by isolates of *O. ulmi*. Solubility of native starch in the media is not the limiting factor for large scale production of modified thermoplastic starch. Mechanical strength of bio-film may be optimized by regulating the drying temperature and drying duration. Different properties of bio-package material for commercial application can be selected for from modified thermoplastic starch. Although only two isolates of *O. ulmi* are demonstrated here, other isolates of this fungus are able to produce modified thermoplastic starch, as all such isolates have a similar genetic makeup. It will be appreciated by those skilled in the art that other variations of the preferred embodiment may also be practised without departing from the scope of the invention.

What is claimed is:

1. A method of manufacture of a modified thermoplastic starch from a native starch using a fungus *Ophiostoma ulmi sensu lata*, comprising the steps of:
   (a) adding the fungus to a fungal growth medium and growing a culture of the fungus in the fungal growth medium as a shake culture at an agitation rate sufficient to optimize fungal growth for a time period of between 0.5 and 10 days until the concentration of spores produced by the fungus is between 0.1 and 10 g/L;

(b) adding the native starch to the fungus culture to form a first mixture;

(c) mixing the first mixture at a mixing rate of between 10 and 1000 rpm and a mixing temperature of between 5° C. and 50° C.; and (d) harvesting the modified thermoplastic starch from the mixture resultant from step (c).

2. The method of manufacture of a modified thermoplastic starch of claim 1, wherein the time period is between 0.5 and 5 days.

3. The method of manufacture of a modified thermoplastic starch of claim 1, wherein the mixing rate is between 10 and 500 rpm.

4. The method of manufacture of a modified thermoplastic starch of claim 1, wherein the mixing temperature is between 5° C. and 40° C.

5. The method of manufacture of a modified thermoplastic starch of claim 1, wherein the native starch is selected from the group comprising native potato starch, native corn starch, and native tapioca starch.

6. The method of manufacture of a modified thermoplastic starch of claim 1, wherein the fungal growth medium is a yeast extract medium.

7. The method of manufacture of a modified thermoplastic starch of claim 6, wherein the yeast extract medium comprises distilled water, yeast extract, $KH_2PO4$, $MgSO_4$, $FeCl_3.6H_2O$, $MnCl_4.H_2O$, $ZnSO_4.7H_2$, O and sucrose.

8. The method of manufacture of the modified thermoplastic starch of claim 1, wherein the harvesting step comprises extracting the modified thermoplastic starch from the mixture resultant from step (c) and lyophilizing the modified thermoplastic starch.

9. The method of manufacture of a modified thermoplastic starch of claim 1, wherein the harvesting step comprises the following steps:
(i) centrifuging the mixture resultant from step (c) at a rotational speed of between 10 and 10000 rpm for a centrifugation period of between 0.5 and 60 minutes at room temperature to obtain a supernatant and a second mixture comprising spores of the fungus and the modified thermoplastic starch;
(ii) decanting the supernatant;
(iii) lyophilizing the second mixture; and
(iv) removing the spores from the lyophilized second mixture thereby providing the modified thermoplastic starch.

10. The method of manufacture of a modified thermoplastic starch of claim 9, wherein the rotational speed is between 200 and 6000 rpm.

11. The method of manufacture of a modified thermoplastic starch of claim 9, wherein the centrifugation period is between 5 and 40 minutes.

12. A method of manufacture of a modified thermoplastic starch from a native starch using a fungus *Ophiostoma ulmi* sensu lata, comprising the steps of:
(a) adding *Ophiostoma ulmi* sensu lata to a yeast extract medium comprised of distilled water, yeast extract, $KH_2PO4$, $MgSO_4$, $FeCl_3.6H_2O$, $MnCl_4.H_2O$, $ZnSO_4.7H_2$, O and sucrose, and growing a culture of *Ophiostoma ulmi* sensu lata in said yeast extract medium as a shake culture at an agitation rate sufficient to optimize fungal growth for a time period of between 0.5 and 10 days until the concentration of spores of the fungus is between 0.5 and 10 g/L;

(b) adding a native starch selected from the group comprising native potato starch, native corn starch, and native tapioca starch to the fungus culture to form a first mixture;

(c) mixing the first mixture at a mixing rate of between 20 and 200 rpm and a mixing temperature of between 10° C. and 40° C. to form a spore culture;

(d) centrifuging the spore culture at a rotational speed of between 1000 and 6000 rpm for a centrifugation period of between 1 and 30 minutes at room temperature to obtain a supernatant and a second mixture comprising spores of the fungus and the modified thermoplastic starch;

(e) decanting the supernatant;

(f) lyophilizing the second mixture; and (g) removing the spores from the lyophilized second mixture thereby obtaining the modified thermoplastic starch.

13. A method of manufacture of a modified thermoplastic starch from a native starch using a fungus *Ophiostoma ulmi* sensu lata, comprising the steps of:
(a) adding the fungus to a fungal growth medium and growing a culture of the fungus in the fungal growth medium as a shake culture at an agitation rate sufficient to optimize fungal growth for a time period of between 0.5 and 10 days until the concentration of spores produced by the fungus is between 0.1 and 10 g/L;
(b) centrifuging the fungus culture to obtain a supernatant;
(c) incubating the supernatant with the native starch for a time period between 0.1 and 4 days to obtain a first mixture;
(d) mixing the first mixture at a mixing rate of between 10 and 1000 rpm and a mixing temperature of between 5° C. and 50° C.; and
(e) harvesting the modified thermoplastic starch from the mixture resultant from step (d).

14. A method of manufacture of a modified thermoplastic starch from a native starch using a fungus *Ophiostoma ulmi* sensu lata, comprising the steps of:
(a) adding the fungus to a fungal growth medium comprising the native starch and growing a culture of the fungus in the fungal growth medium as a shake culture at an agitation rate and time sufficient to optimize fungal growth until the concentration of spores produced by the fungus is between 0.1 and 10 g/L;
(b) centrifuging the fungal culture to obtain a supernatant;
(c) adding ethanol to the supernatant;
(d) centrifuging the mixture resultant from step (c) to obtain thermoplastic starch as a precipitate; and
(e) isolating the thermoplastic starch.

15. The method of manufacture of claim 14 wherein the time of culturing is for a period of between 0.5 and 10 days.

16. A method of manufacture of a biodegradable product made from a modified thermoplastic starch from a native starch using a fungus *Ophiostoma ulmi* sensu lata, comprising the steps of:
(a) adding the fungus to a fungal growth medium and growing a culture of the fungus in the fungal growth medium as a shake culture at an agitation rate sufficient to optimize fungal growth for a time period of between 0.5 and 10 days until the concentration of spores produced by the fungus is between 0.1 and 10 g/L;
(b) adding the native starch to the fungus culture to form a first mixture;
(c) mixing the first mixture at a mixing rate of between 10 and 1000 rpm and a mixing temperature of between 5° C. and 50° C.;

(d) harvesting the modified thermoplastic starch from the mixture resultant from step (c);
(e) manufacturing the harvested thermoplastic starch to obtain a biodegradable product selected from the group consisting of a film, a packaging film, a laminate, a foamed molded article, an insulation material and a filled molded article.

17. A method of manufacture of a biodegradable product made from a modified thermoplastic starch from a native starch using a fungus *Ophiostoma ulmi* sensu lata, comprising the steps of:
(a) adding the fungus to a fungal growth medium and growing a culture of the fungus in the fungal growth medium as a shake culture at an agitation rate sufficient to optimize fungal growth for a time period of between 0.5 and 10 days until the concentration of spores produced by the fungus is between 0.1 and 10 g/L;
(b) adding the native starch to the fungus culture to form a first mixture;
(c) mixing the first mixture at a mixing rate of between 10 and 1000 rpm and a mixing temperature of between 5° C. and 50° C.;
(d) harvesting the modified thermoplastic starch from the mixture resultant from step (c);
(e) combining the harvested modified thermoplastic starch with glycerol and water in a container;
(f) heating the contained mixture in a water bath at a temperature of about 30° C. for a heating period of at least 15 minutes while maintaining constant volume, to form a solution; and
(g) heating the solution at a drying temperature of at least 30° C. until a dry plastic is obtained.

18. The method of manufacture of the biodegradable plastic of claim 17, wherein the bath temperature in step (b) is at least 70° C.

19. The method of manufacture of a biodegradable plastic of claim 17, wherein the heating period of step (b) is about 1 hour.

20. The method of manufacture of a biodegradable plastic of claim 17, wherein the drying temperature in step (c) is at least 50° C.

* * * * *